(12) United States Patent
Matthews

(10) Patent No.: US 8,229,679 B1
(45) Date of Patent: Jul. 24, 2012

(54) STEPPED CHIRP LIDAR SYSTEM AND METHOD

(75) Inventor: Grant Matthews, Ft. Wayne, IN (US)

(73) Assignee: Exelis, Inc., McLeans, VA (US)

( * ) Notice: Subject to any disclaimer, the term of this patent is extended or adjusted under 35 U.S.C. 154(b) by 354 days.

(21) Appl. No.: 12/558,899

(22) Filed: Sep. 14, 2009

(51) Int. Cl.
*G01N 33/24* (2006.01)

(52) U.S. Cl. .......... 702/24; 250/343; 356/437; 356/432; 398/25; 398/26; 398/27

(58) Field of Classification Search .............. 702/24; 250/221, 227.12, 343; 356/484, 437, 432, 356/438, 311, 323; 359/325, 326; 372/29.02, 372/29.023, 99, 43.01, 50.11; 257/E33.01, 257/E33.067; 324/307; 398/25, 26, 27

See application file for complete search history.

(56) References Cited

U.S. PATENT DOCUMENTS

| | | | | |
|---|---|---|---|---|
| 3,311,834 A * | 3/1967 | Barker | | 315/360 |
| 5,218,416 A | 6/1993 | Haring et al. | | |
| 6,111,640 A | 8/2000 | Hedman et al. | | |
| 6,913,735 B2 * | 7/2005 | Imasaki et al. | | 422/186 |
| 6,995,846 B2 * | 2/2006 | Kalayeh et al. | | 356/437 |
| 7,145,713 B2 * | 12/2006 | Chang et al. | | 359/325 |
| 7,148,469 B2 * | 12/2006 | Pearson | | 250/227.12 |
| 7,361,922 B2 * | 4/2008 | Kameyama et al. | | 250/574 |
| 7,616,888 B2 * | 11/2009 | Mendenhall et al. | | 398/25 |
| 7,705,988 B2 * | 4/2010 | Richman | | 356/437 |
| 7,995,917 B2 * | 8/2011 | Mendenhall et al. | | 398/25 |
| 2005/0041253 A1 * | 2/2005 | Pearson | | 356/484 |
| 2005/0100336 A1 * | 5/2005 | Mendenhall et al. | | 398/27 |
| 2006/0012797 A1 * | 1/2006 | Chang et al. | | 356/484 |
| 2009/0002680 A1 * | 1/2009 | Ruff et al. | | 356/5.09 |
| 2010/0070199 A1 * | 3/2010 | Mendenhall et al. | | 702/28 |
| 2010/0279446 A1 * | 11/2010 | Henrichs | | 438/31 |

* cited by examiner

*Primary Examiner* — Carol Tsai
(74) *Attorney, Agent, or Firm* — RatnerPrestia

(57) ABSTRACT

A system assesses a column of gas in an atmosphere. The system includes an optical transmitter for transmitting (a) an online signal tuned to an online wavelength of gas, (b) an offline signal tuned to an offline wavelength of the gas, and (c) an optical signal for providing altimetry data. A modulator is included for modulating the online signal with a first stepped chirp waveform and modulating the offline signal with a second stepped chirp waveform. A processor assesses the column of gas, after receiving a returned online signal, a returned offline signal and a returned optical signal. A lock-in amplifier is included for (a) multiplying a returned signal with the first stepped chirp waveform to obtain a detected online signal, and (b) multiplying the returned signal with the second stepped chirp waveform to obtain a detected offline signal. The processor is configured to remove ground reflections from the optical signal to obtain scattered noise, and assess the column of gas based on the scattered noise. The processor is also configured to (a) multiply an estimated returned online signal with the first stepped chirp waveform to obtain a simulated cloud only online signal, and (b) multiply an estimated returned offline signal with the second stepped chirp waveform to obtain a simulated cloud only offline signal. In addition, the processor is configured to assess the column of gas by performing regression between the detected online and offline signals and the simulated online and offline signals.

18 Claims, 10 Drawing Sheets

STEPPED CHIRP LIDAR SYSTEM AND METHOD

FIELD OF THE INVENTION

The invention relates generally to the field of spectroscopic analysis using a lidar (light detection and ranging) system. More specifically, the present invention relates to spectroscopic analysis of a column of gas disposed in the earth's atmosphere using a stepped chirp lidar system.

BACKGROUND OF THE INVENTION

The Active Sensing of CO2 Emissions over Nights, Days, and Seasons (ASCENDS) mission is a CO2 sensing project that uses a lidar system. The requirement of the mission is to accurately map sources, sinks and concentrations of global CO2 levels across the globe. The lidar system relies on the ratio between light scattered from the ground at two slightly different wavelengths around the 1.57 μm is CO2 absorption line. One wavelength is tuned to the peak of this absorption and is referred to as "online". The other is positioned slightly away from this spectral peak and is referred to as "offline". Using the ratio of light scattered from the ground at these two wavelengths it is possible to obtain the column integrated CO2 within the atmosphere.

A continuous wave (CW) solid state laser concept has been developed for the ASCENDS mission. Its advantage over a pulsed laser system is an expected longer lifetime as it utilizes more reliable technology, such as that used in the telecommunications industry. However, a pulsed laser concept has an advantage that the effects of cloud scattering may be more easily separated from the ground scattered signal. For a CW system, light scattered from clouds represents noise in the CO2 retrieval, as the light passes through a smaller path length than that scattered from the ground. This may lead to an underestimate of the column density.

The present invention, as will be explained, includes a new signal processing concept for a CW lidar system that removes the cloud scatter noise signal. The present invention includes a chirp pulsed waveform in which the frequency sweep is stepped in time, rather than linearly varied in time.

SUMMARY OF THE INVENTION

To meet this and other needs, and in view of its purposes, the present invention provides a system for assessing a column of gas in an atmosphere. The system includes an optical transmitter for transmitting (a) an online signal tuned to an online wavelength of gas, (b) an offline signal tuned to an offline wavelength of the gas, and (c) an optical signal for providing altimetry data. A modulator is included for modulating the online signal with a first stepped chirp waveform and modulating the offline signal with a second stepped chirp waveform. A processor assesses the column of gas, after receiving a returned online signal, a returned offline signal and a returned optical signal.

The system includes a lock-in amplifier for (a) multiplying a returned signal with the first stepped chirp waveform to obtain a detected online signal, and (b) multiplying the returned signal with the second stepped chirp waveform to obtain a detected offline signal.

The processor is configured to remove ground reflections from the optical signal to obtain scattered noise, and assess the column of gas based on the scattered noise. The processor is also configured to (a) multiply an estimated returned online signal with the first stepped chirp waveform to obtain a simulated cloud only online signal, and (b) multiply an estimated returned offline signal with the second stepped chirp waveform to obtain a simulated cloud only offline signal. In addition, the processor is configured to assess the column of gas by performing regression between the detected online and offline signals and the simulated online and offline signals.

The first and second stepped chirp waveforms each includes finite steps, each step having a period sufficiently long to allow for travel time to a ground surface and sampling time of return signals. The first and second stepped chirp waveforms each includes a frequency change based on a sampling frequency divided by a base 2 sampling pack. The first and second stepped chirp waveforms each includes a sawtooth waveform having a period of approximately 0.25 seconds. The first and second stepped chirp waveforms are synchronized to each other.

The optical transmitter of the system includes an online laser for transmitting the online signal, an offline laser for transmitting the offline signal, and a pseudo random noise (PN) modulator for modulating the offline laser to transmit the optical signal.

The system includes a reference detector for sampling the online and offline signals upon transmission and obtaining a first ratio between the online and offline signals emitted from the optical transmitter ($I_o^{on}$ and $I_o^{off}$). The processor is configured to (a) determine scattered noise returned by the optical signal, (b) determine a second ratio between the online and offline signals returned from ground ($I_g^{on}$ and $I_g^{off}$), based on the scattered noise, and obtain density of the column of gas by multiplying the first ratio with the second ratio.

The present invention includes a method of assessing a column of gas between an airborne platform and the earth. The method includes the steps of:

(a) transmitting an online optical signal modulated by a first stepped chirp waveform;

(b) transmitting an offline optical signal modulated by a second stepped chirp waveform;

(c) transmitting an optical signal modulated by a pseudo random noise (PN) waveform;

(d) determining scattered noise returned by the PN modulated optical signal; and (e) assessing the column of gas, based on the modulated online and offline optical signals and the scattered noise returned by the PN modulated optical signal.

Determining the scattered noise includes receiving the PN modulated optical signal including a ground return component and scattered noise from clouds, and removing the ground return component.

Steps (a) and (b) of the method includes modulating the online and offline optical signals with the first and second stepped chirp waveforms, respectively, each waveform having a step sufficiently long to allow for travel time to a ground surface and sampling time of return signals. Each waveform includes a stepped frequency sweep of approximately 25 KHz to 75 KHz.

Assessing the column of gas includes convolving the modulated online and offline optical signals with the scattered noise returned by the PN modulated optical signal.

Another embodiment of the present invention includes a method of assessing a column of gas through the atmosphere, including layers of clouds. The method includes the steps of:

(a) transmitting, by a lidar system, an online signal having a wavelength absorbed by a gas and an offline signal having a wavelength not absorbed by the gas, in which the online signal is modulated by a first stepped chirp waveform and the offline signal is modulated by a second stepped chirp waveform;

(b) transmitting a PN modulated optical signal having an offline wavelength not absorbed by the gas;

(c) determining emitted radiances of the online signal and the offline signal, as $I_0^{on}$ and $I_0^{off}$, respectively;

(d) determining scattered noise returned from the layers of clouds by the transmitted PN modulated optical signal, as P'(t);

(e) determining received radiances of the online signal and the offline signal during each chirp step of the first and second stepped chirp waveforms, respectively, as $M_{on}^P$ and $M_{off}^P$;

(f) estimating radiances of the online signal and the offline signal during each chirp step of the first and second stepped chirp waveforms, respectively, as $K_{on}^P$ and $K_{off}^P$;

(g) regressing the $K_{on}^P$ and $K_{off}^P$ signals against the $M_{on}^P$ and $M_{off}^P$ signals, respectively;

(h) determining radiances from the ground for the online and offline signals, respectively, as $I_g^{on}$ and $I_g^{off}$, based on step (g); and (i) characterizing the column of gas, after performing step (h).

Step (f) of estimating includes convolving the scattered noise returned from the layers of clouds with (i) an estimated returned online signal, and (ii) an estimated returned offline signal.

The first and second stepped chirp waveforms includes a sawtooth, which is cycled at approximately 4 Hz.

It is understood that the foregoing general description and the following detailed description are exemplary, but are not restrictive, of the invention.

BRIEF DESCRIPTION OF THE FIGURES

The invention may be understood from the following detailed description when read in connection with the accompanying figures.

DETAILED DESCRIPTION OF THE INVENTION

Figure 1:
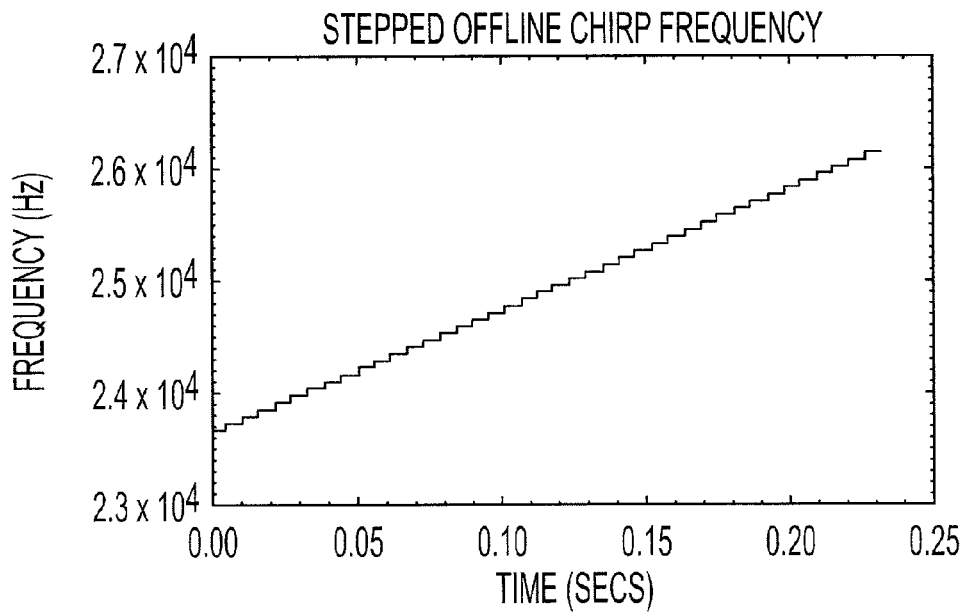
FIG. 1(a) shows an exemplary offline stepped chirp frequency sweep around 25 KHz, in accordance with an embodiment of the present invention.
FIG. 1(b) shows an exemplary online stepped chirp frequency sweep around 50 KHz, in accordance with an embodiment of the present invention.
FIG. 1(c) shows an exemplary step of the chirp frequency sweep shown in FIGS. 1(a) and 1(b), which has a step length sufficiently long for atmospheric travel time and a base 2 sampling period, in accordance with an embodiment of the present invention.
FIG. 1(d) depicts an exemplary atmospheric scattering profile, R(t), which is returned from cloud layers and the ground surface.
Figure 1:
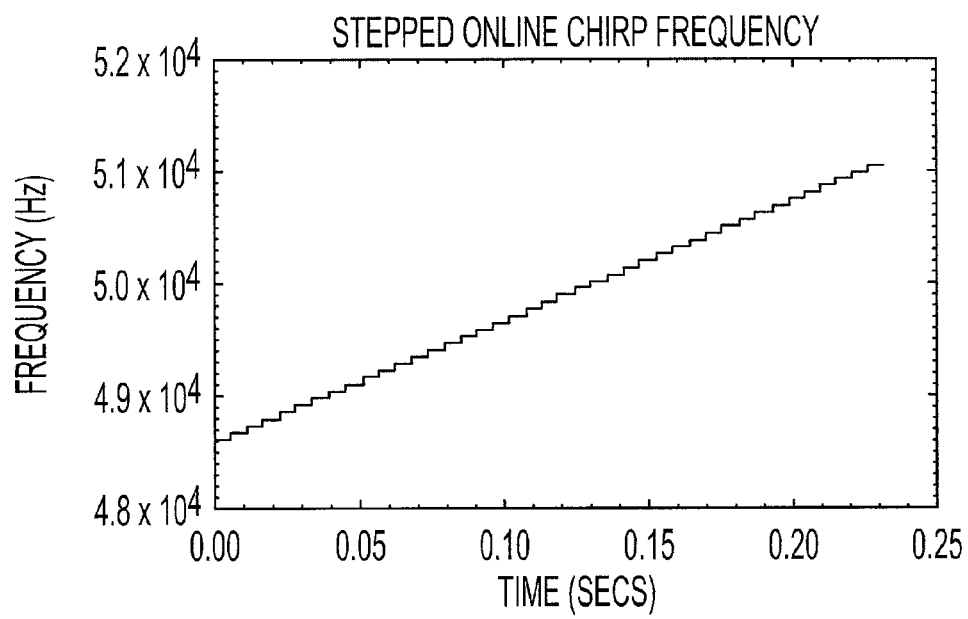
Figure 1:
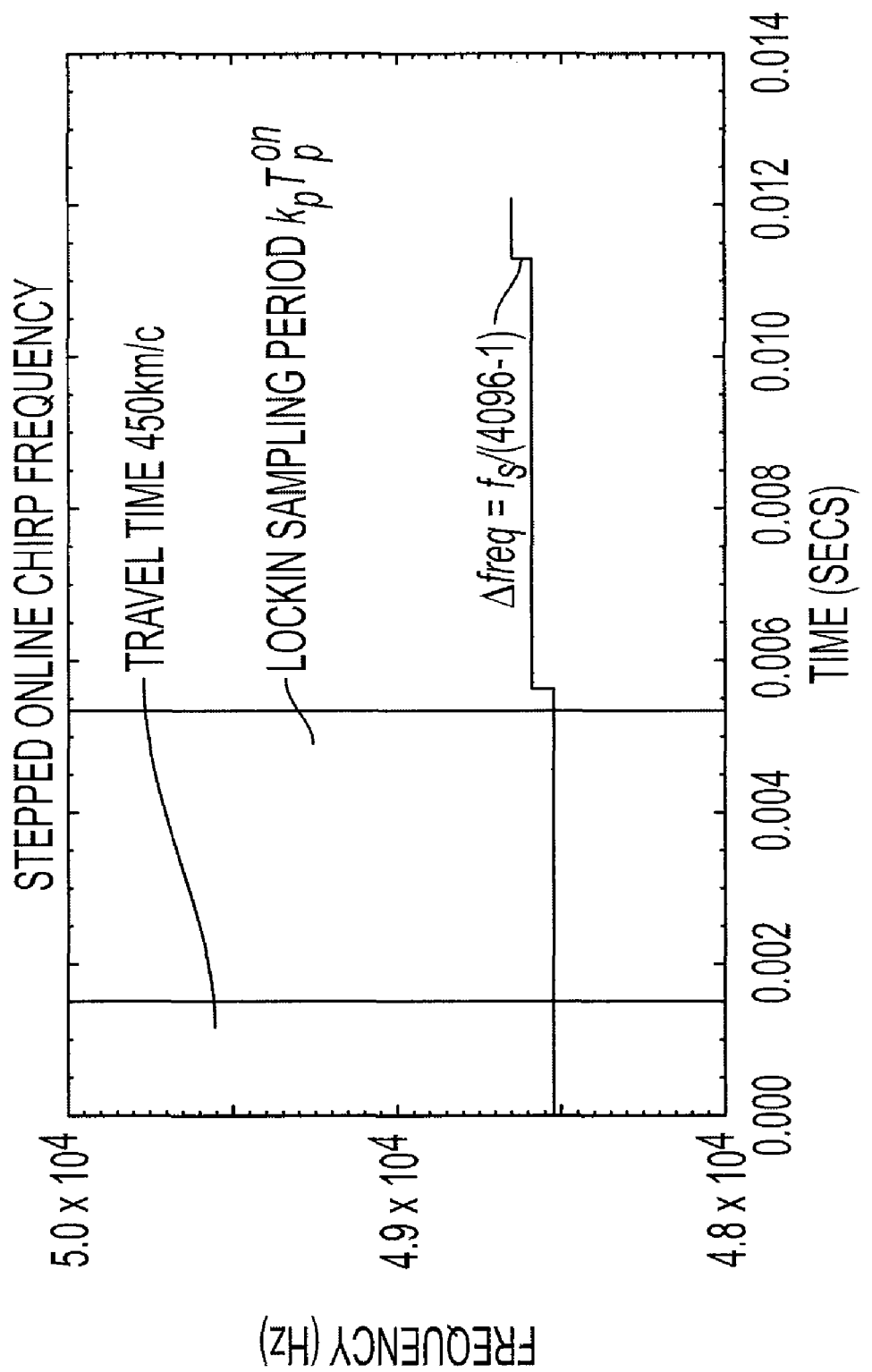
Figure 1:
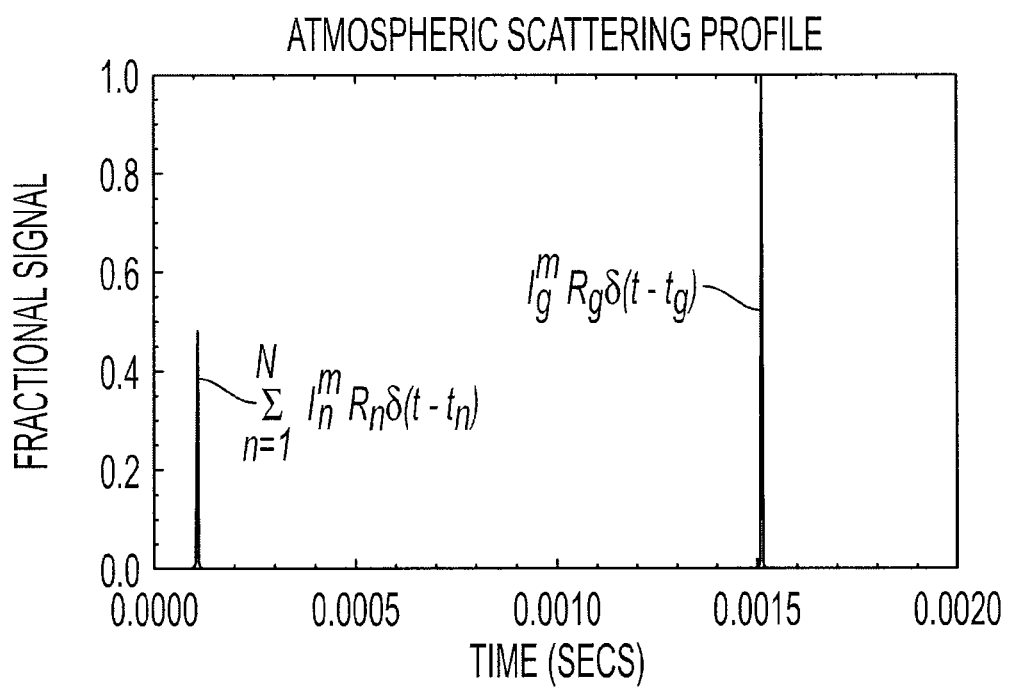

Generally, the atmosphere may be represented in one dimension with multiple cloud scattering layers in addition to the ground. Transmitted lidar light encounters each scattering layer $R_n$ at time $t_n$, as shown in FIG. 1(d). Thus, a CW lidar signal, y(t), modulated at frequency $\omega_m$, produces a return signal Y(t) given by Eqn. 4:

$$R(t) = I_g^m R_g \delta(t - t_g) + \sum_{n=1}^{N} I_n^m R_n \delta(t - t_n) \tag{1}$$

$$y(t) = A + B\cos(\omega_m t + \phi_m) \tag{2}$$

$$Y(t) = \int_0^t R(t')y(t'-t)dt' \tag{3}$$

$$= I_g^m R_g [A + B\cos(\omega_m(t-t_g) + \phi_m)] + \tag{4}$$
$$\sum_{n=1}^{N} I_n^m R_n [A + B\cos(\omega_m(t-t_n) + \phi_m)]$$

where $I_n^m$ is the modulated lidar radiance that passes through the atmosphere, to and from the reflective layer $R_n$. Determination of the column integrated $CO_2$ requires measurements of the radiance $I_g^m$ from the ground reflective layer $R_g$. The radiance passes twice through the entire atmosphere, from the satellite at altitude $Z_s$, to the surface at $Z_g$, as follows:

$$I_g^m = I_0^m \times \exp\left(2\int_{z_s}^{z_g} \alpha_m(z)dz\right) \tag{5}$$

Equation (5) expresses the atmospheric optical depth at the chosen wavelength (for example, either $CO_2$ online $\alpha_{on}(z)$, or offline $\alpha_{off}(z)$ in Eqn. 5). The ratio $I_0^{on}/I_0^{off}$ is determined by a reference detector that samples the online and offline laser signals upon emission. Next, the result of Eqn. 6 is found, giving an accurate determination of column integrated $CO_2$:

$$\frac{I_g^{on} I_0^{off}}{I_g^{off} I_0^{on}} = \exp\left(2\int_{z_s}^{z_g} \alpha_{on}(z) - \alpha_{off}(z)dz\right) \tag{6}$$

In an ideal situation, where there are no clouds, the only reflective surface is $R_g$. Thus, separation of $I_g^{on}$ and $I_g^{off}$ from the return signal may be achieved by modulating the online and offline radiances at different frequencies, $\omega_{on}$ and $\omega_{off}$. The second term in Eqns. 1 and 4 becomes zero and the time of ground reflection $t_g$ may be determined from altimetry data.

A lock-in amplifier with phase sensitive detection may be used to pick out the online and offline signals by multiplying the return signals with the generated modulation signals $L^{on}(t)$ and $L^{off}(t)$ before integrating, as follows:

$$L^{on}(t) = C \cdot \cos(\omega_{on}(t-t_g) + \phi_m) \tag{7}$$

$$L^{off}(t) = C \cdot \cos(\omega_{off}(t-t_g) + \phi_m) \tag{8}$$

$$R(t) = (I_g^{on} + I_g^{off})R_g \delta(t-tg) \tag{9}$$

$$y(t) = A + B[\cos(\omega_{on}t + \phi_m) + \cos(\omega_{off}t + \phi_m)] \tag{10}$$

$$Y(t) = I_g^{on} R_g [A + B\cos(\omega_{on}(t-t_g) + \phi_m)] + I_g^{off} R_g [A + B\cos(\omega_{off}(t-t_g) + \phi_1] \tag{11}$$

$$M_{on} = \frac{1}{k\tau^{on}} \int_0^{\tau_0 + k\tau^{on}} Y(t) L^{on}(t) dt \tag{12}$$

$$= C \cdot B \cdot I_g^{on} R_g / 2 \tag{13}$$

$$M_{off} = \frac{1}{k\tau^{off}} \int_0^{\tau_0 + k\tau^{off}} Y(t) L^{off}(t) dt \tag{14}$$

$$= C \cdot B \cdot I_g^{off} R_g / 2 \tag{15}$$

$$\frac{M_{on} I_0^{off}}{M_{off} I_0^{on}} = \exp\left(2 \int_{z_s}^{z_g} \alpha_{on}(z) - \alpha_{off}(z) dz\right) \tag{16}$$

where k is an integer and $\tau^m$ is the modulation period of the online or offline signal (note $\omega_{on} \neq \omega_{off}$). Note that a period (.) in Equations (13) and (15) is a multiplication sign.

The integrations in Eqns. 12 and 14 yield good signal to noise in the results. Accordingly, in a clear sky situation, retrieval of Eqn. 16 is possible. However, in the presence of clouds or aerosol layers, the retrieval of Eqn. 16 is not possible, because scattering from multiple atmospheric layers adds considerable noise to the retrieval process, even after use of a lock in amplifier.

As will now be explained, the present invention includes a stepped frequency chirp CW lidar system, in order to remove atmospheric scattering noise from cloud layers. In addition, the stepped chirp CW lidar system is accompanied by an altimetry system, which is used to provide accurate knowledge of the atmospheric scattering profile $R_{(t)}$. In order to maximize the altimetry signal, the wavelength of the altimetry system is set to an offline wavelength. The offline wavelength of the altimetry system is set to the same wavelength as the offline signal of the CW lidar system.

Hence, the altimetry data P(t) is available for each frequency sweep such that:

$$P(t) = U \cdot R(t) + w(t) \tag{17}$$

$$= U \cdot I_g^{off} R_g \delta(t - t_g) + w(t) + U \times \sum_{n=1}^{N} I_n^{off} R_n \delta(t - t_n) \tag{18}$$

where w(t) is a random noise component and U is a linear scaling factor to the true atmospheric profile. Note that a period (.) in Equations (17) and (18) is a multiplication sign.

Referring next to FIGS. 1(a) and 1(b), the stepped offline chirp frequency and the stepped online chirp frequency sweep signals are shown therein. The stepped offline chirp frequency sweep is used to modulate the offline optical signal, and the stepped online chirp frequency sweep is used to modulate the online optical signal. Both sweeps are identical to each other and synchronized by the same clock. Both sweeps, however, are centered about a different frequency, for example, 25 KHz and 50 KHz; and the length of one sweep is the same as the length of the other sweep. Thus, in a graphical presentation, one sweep may be positioned above the other sweep. In this manner, a frequency step of the offline sweep is in alignment with a corresponding frequency step of the online sweep.

As shown, both sweeps are performed in finite steps, each lasting a period η which is long enough to allow for travel time to the earth's surface at $t_g$ (450 km/c) and an integer k times the period $\tau^m$ of the modulation for that chirp step. The shift in frequency with each step is fixed based on a sampling frequency, $f_s$, so that $$\Delta \text{freq} = f_s/(4096-1)$$

where $f_s$ is 1 MHz (for example) and 4096 is a base 2 sampling pack (for example).

The step of the sweep is best shown in FIG. 1(c). Because each step of the sweep is changed in time, the frequency of the modulation has a time dependence $\omega_m \rightarrow \omega_m(t)$. The time dependence of the modulation may be expressed as follows:

$$L^{on}(t) = C \cdot \cos(\omega_{on}(t-t_g)(t-t_g) + \phi_m) \tag{19}$$

$$L^{off}(t) = C \cdot \cos(\omega_{off}(t-t_g)(t-t_g) + \phi_m) \tag{20}$$

$$R(t) = (I_g^{on} + I_g^{off})R_g \delta(t - tg) + \sum_{n=1}^{N} (I_n^{on} + I_n^{off}) R_n \delta(t - t_n) \tag{21}$$

$$y(t) = A + B[\cos(\omega_{on}(t)t + \phi_m) + \cos(\omega_{off}(t)t + \phi_m)] \tag{22}$$

$$Y(t) = I_g^{on} R_g [A + B\cos(\omega_{on}(t - t_g)(t - t_g) + \phi_m)] + \\ I_g^{off} R_g [A + B\cos(\omega_{off}(t - t_g)(t - t_g) + \phi_m)] + \\ \sum_{n=1}^{N} I_n^{on} R_n [A + B\cos(\omega_{on}(t - t_n)(t - t_n) + \phi_m)] + \\ \sum_{n=1}^{N} I_n^{off} R_n [A + B\cos(\omega_{off}(t - t_n)(t - t_n) + \phi_m)] \tag{23}$$

$$M_{on}^p = \frac{1}{k_p \tau_p^{on}} \int_{p \cdot \eta + t_0}^{p \cdot \eta + t_0 + k_p \tau_p^{on}} Y(t) L^{on}(t) dt \tag{24}$$

$$= C \cdot B \cdot I_g^{on} R_g / 2 + \tag{25}$$

$$C \cdot B \sum_{n=1}^{N} \frac{I_n^{on} R_n}{k_p \tau_p^{on}} \int_{p \cdot \eta + t_0}^{p \cdot \eta + t_0 + k_p \tau_p^{on}} \cos(\omega_{on}(t - t_n)(t - t_n) + \phi_m) \\ \cos(\omega_{on}(t - t_g)(t - t_g) + \phi_m) dt$$

$$M_{off}^p = \frac{1}{k_p \tau_p^{off}} \int_{p \cdot \eta + t_0}^{p \cdot \eta + t_0 + k_p \tau_p^{off}} Y(t) L^{off}(t) dt \tag{26}$$

$$= C \cdot B \cdot I_g^{off} R_g / 2 + \qquad (27)$$

$$C \cdot B \sum_{n=1}^{N} \frac{I_n^{off} R_n}{k_p \tau_p^{off}} \int_{p \cdot \eta + t_0}^{p \cdot \eta + t_0 + k_p \tau_p^{off}} \cos(\omega_{off}(t - t_n)(t - t_n) + \phi_m)$$

$$\cos(\omega_{off}(t - t_g)(t - t_g) + \phi_m) dt$$

Thus, the lock in integrated online and offline signal $M_m^p$ from each chirp step 'p' is given by Eqns. 25 and 27, respectively. In each equation, the first term represents the desired ground signal, and the second term represents the scattered noise from the cloud layers. Note that a period (.) in the above equations is a multiplication sign.

Figure 2:
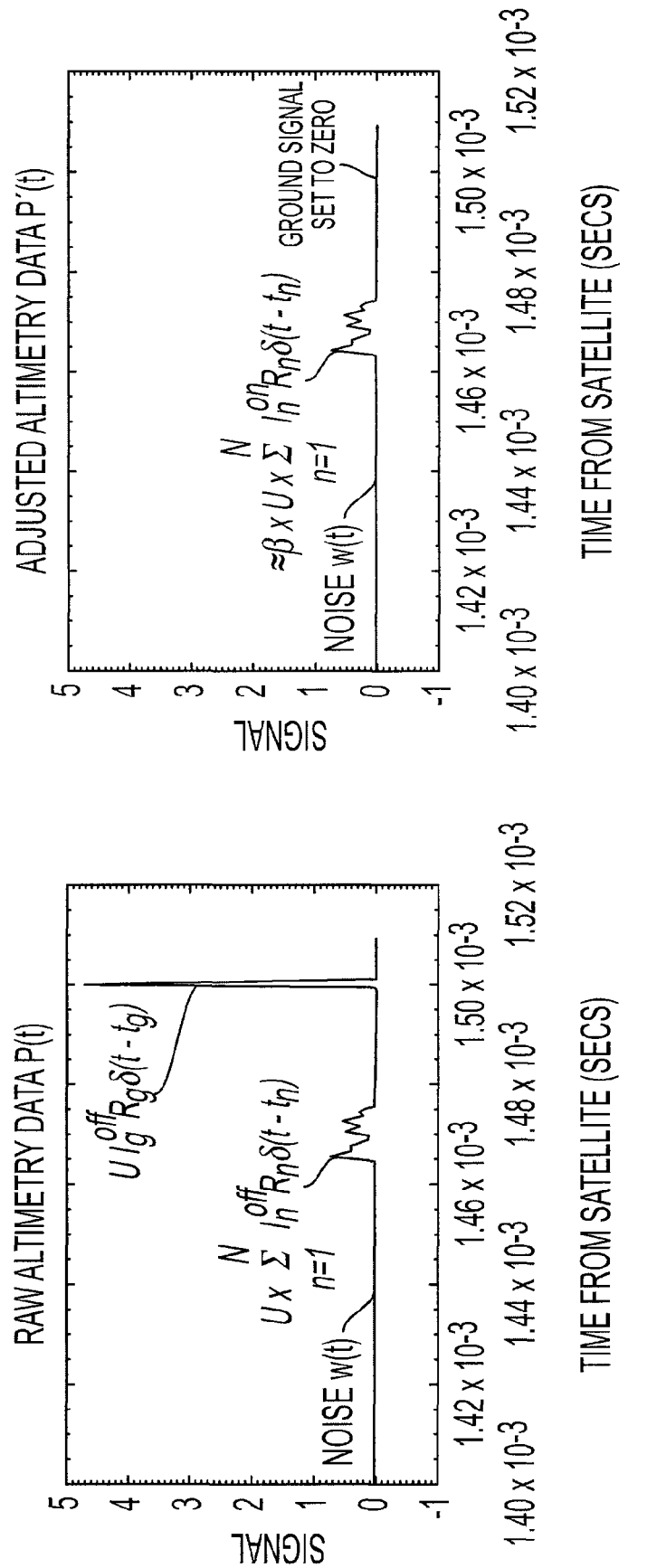
FIG. 2(a) shows an exemplary profile of raw offline altimetry data returned from a cloud layer and the ground surface.
FIG. 2(b) shows adjusted altimetry data, after the ground reflection is removed from the profile shown in FIG. 2(a), in accordance with an embodiment of the present invention.

The present invention includes the altimetry data P(t), in order to simulate the variation of this noise with each chirp step. This requires removal of the ground signal at $t_g$ from the altimetry data. The altimetry data with the ground signal removed is expressed as P'(t) (i.e. set $P(t_g)=0$), as shown in FIGS. 2(a) and 2(b).

Assuming that the cloud layer is high (e.g. Cirrus clouds) and localized around a general location t=Y, then the approximation of Eqn. 29 may be made, as follows:

$$P'(t) = w(t) + U \times \sum_{n=1}^{N} I_n^{off} R_n \delta(t - t_n) \qquad (28)$$

$$\approx w(t) + \beta \times U \times \sum_{n=1}^{N} I_n^{on} R_n \delta(t - t_n) \qquad (29)$$

$$\beta = \exp\left(2 \int_0^{Y \cdot c} \rho_{off}(z) - \rho_{on}(z) dz\right) \qquad (30)$$

where $\rho_{on}$ and $\rho_{off}$ are the online and offline atmospheric absorption for the region above the cloud layers.

The altimetry data of P'(t) may then be convolved with known estimates of the stepped chirp signal from Eqn. 33. This is done before a simulated lock in integration is performed, as shown in Eqns. 34 and 36, with the lock in signal estimates $L_e^{on}(t)$ and $L_e^{off}(t)$ (Eqns. 31 and 32) as follows:

$$L_e^{on}(t) = D \cdot \cos(\omega_{on}(t-t_g)(t-t_g) + \phi_m) \qquad (31)$$

$$L_e^{off}(t) = D \cdot \cos(\omega_{off}(t-t_g)(t-t_g) \phi_m) \qquad (32)$$

$$y'(t) = G + H[\cos(\omega_{on}(t)t + \phi_m) + \cos(\omega_{off}(t)t + \phi_m)] \qquad (33)$$

$$K_{on}^p = \frac{1}{k_p \tau_p^{on}} \int_{p \cdot \eta + t_0}^{p \cdot \eta + t_0 + k_p \tau_p^{on}} \int_0^t P'(t') y'(t'-t) dt' L_e^{on}(t) dt \qquad (34)$$

$$= U \cdot D \cdot H \cdot \beta \times \qquad (35)$$

$$\sum_{n=1}^{N} \frac{I_n^{on} R_n}{k_p \tau_p^{on}} \int_{p \cdot \eta + t_0}^{p \cdot \eta + t_0 + k_p \tau_p^{on}} \cos(\omega_{on}(t-t_n)(t-t_n) + \phi_m)$$

$$\cos(\omega_{on}(t-t_g)(t-t_g) + \phi_m) dt + W_{on}^p$$

$$K_{off}^p = \frac{1}{k_p \tau_p^{off}} \int_{p \cdot \eta + t_0}^{p \cdot \eta + t_0 + k_p \tau_p^{off}} \int_0^t P'(t') y'(t'-t) dt' L_e^{off}(t) dt \qquad (36)$$

$$= U \cdot D \cdot H \times \qquad (37)$$

$$\sum_{n=1}^{N} \frac{I_n^{off} R_n}{k_p \tau_p^{off}} \int_{p \cdot \eta + t_0}^{p \cdot \eta + t_0 + k_p \tau_p^{off}} \cos(\omega_{off}(t-t_n)(t-t_n) + \phi_m)$$

$$\cos(\omega_{off}(t-t_g)(t-t_g) + \phi_m) dt + W_{off}^p$$

The simulated results of $K_{on}^p$ and $K_{off}^p$ are produced with the form shown in Eqns. 35 and 37. The terms $W_{on}^p$ and $W_{off}^p$ are random noise terms resulting from the convolution of noise w(t) with the estimated stepped chirp and lock in signals. Note that a period (.) in the above equations is a multiplication sign.

If the noise terms are neglected, comparison of the simulated results $K_{on}^p$ and $K_{off}^p$ of Eqns. 35 and 37 with the actual derived signals $M_{on}^p$ and $M_{on}^p$ from Eqns. 25 and 27 shows that the two are linearly related as follows:

$$M_{on}^p = \frac{C \cdot B}{U \cdot D \cdot H \cdot \beta} K_{on}^p + \frac{C \cdot B \cdot I_g^{on} R_g}{2} \qquad (38)$$

$$M_{off}^p = \frac{C \cdot B}{U \cdot D \cdot H} K_{off}^p + \frac{C \cdot B \cdot I_g^{off} R_g}{2} \qquad (39)$$

Figure 3:
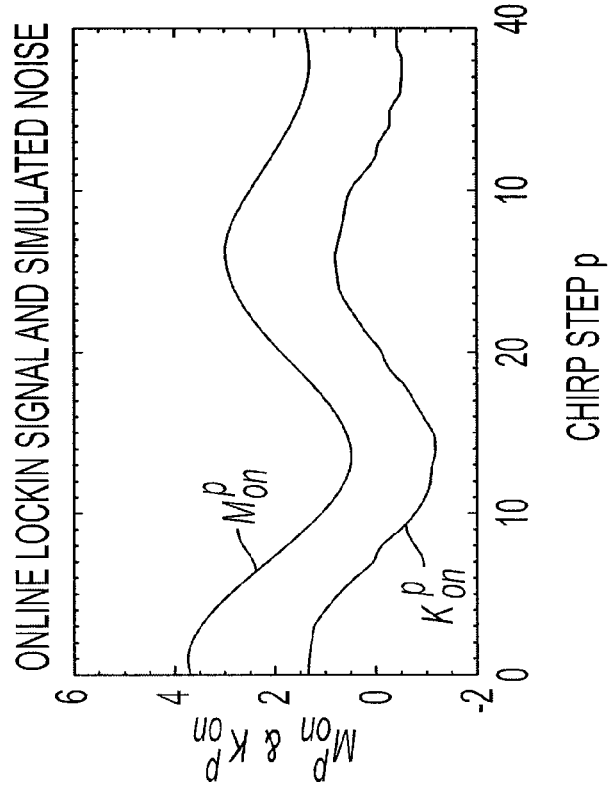
FIG. 3(a) shows an exemplary offline lock in signal, in comparison with altimeter simulated noise, $K_{off}^P$, in accordance with an embodiment of the present invention.
FIG. 3(b) shows an exemplary online lock in signal, $M_{on}^P$, in comparison with altimeter simulated noise, $K_{on}^P$, in accordance with an embodiment of the present invention.
FIG. 3(c) shows an example of linear regression between $M_{off}^P$ and $K_{off}^P$ in accordance with an embodiment of the present invention.
FIG. 3(d) shows an example of a linear regression between $M_{on}^P$ and $K_{on}^P$, in accordance with an embodiment of the present invention.
Figure 3:
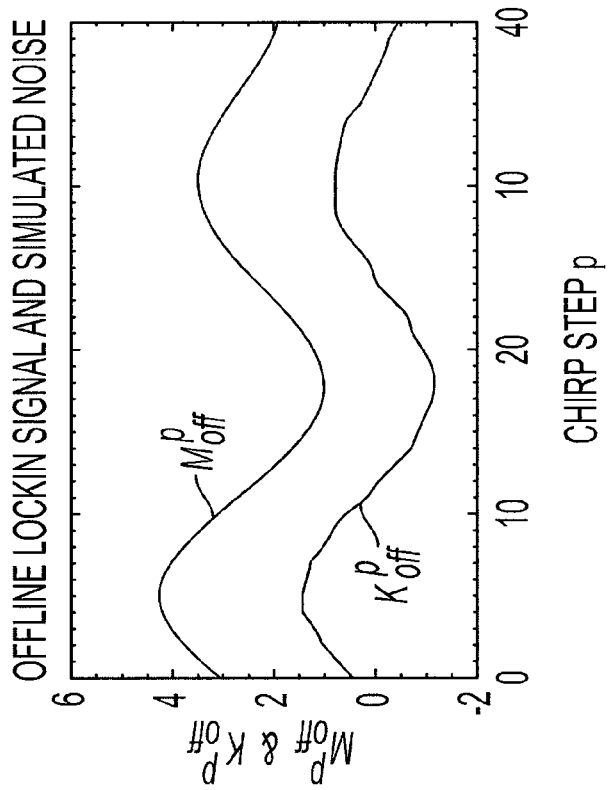
Figure 3:
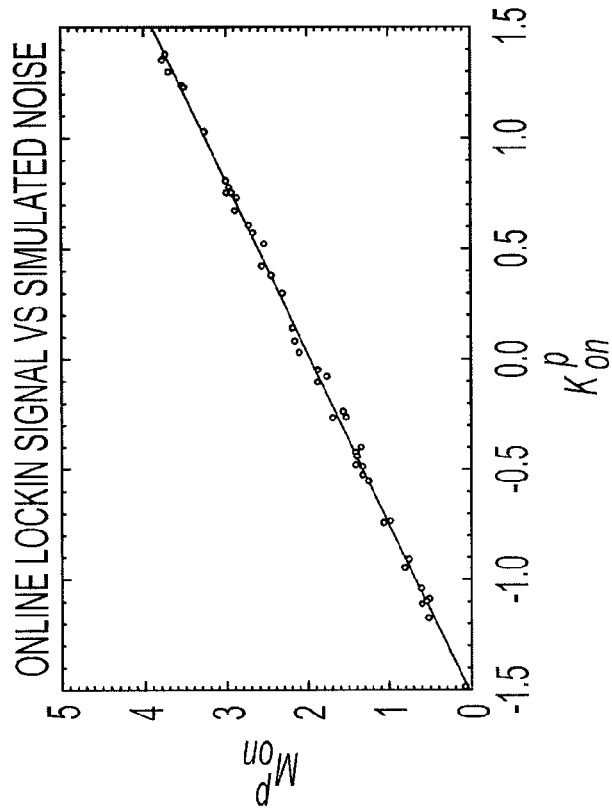
Figure 3:
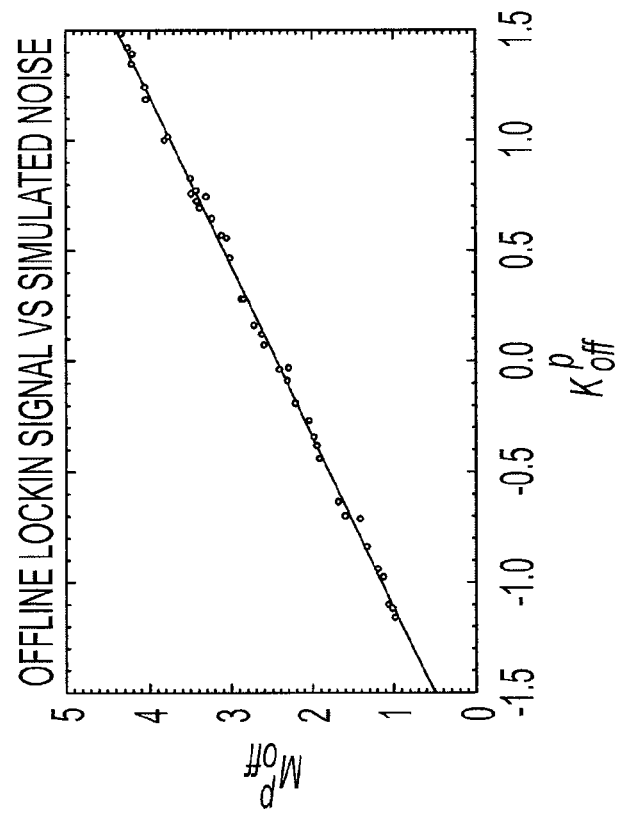

This is graphically illustrated in modeling results, illustrated in FIGS. 3(a) and 3(b), which show the offline and online signals with the simulated noise results. FIGS. 3(c) and 3(d) show linear regressions of the data and simulated noise. The ratio of the intercepts from these regressions is used to derive the desired result of $I_g^{on}/I_g^{off}$.

Figure 4:
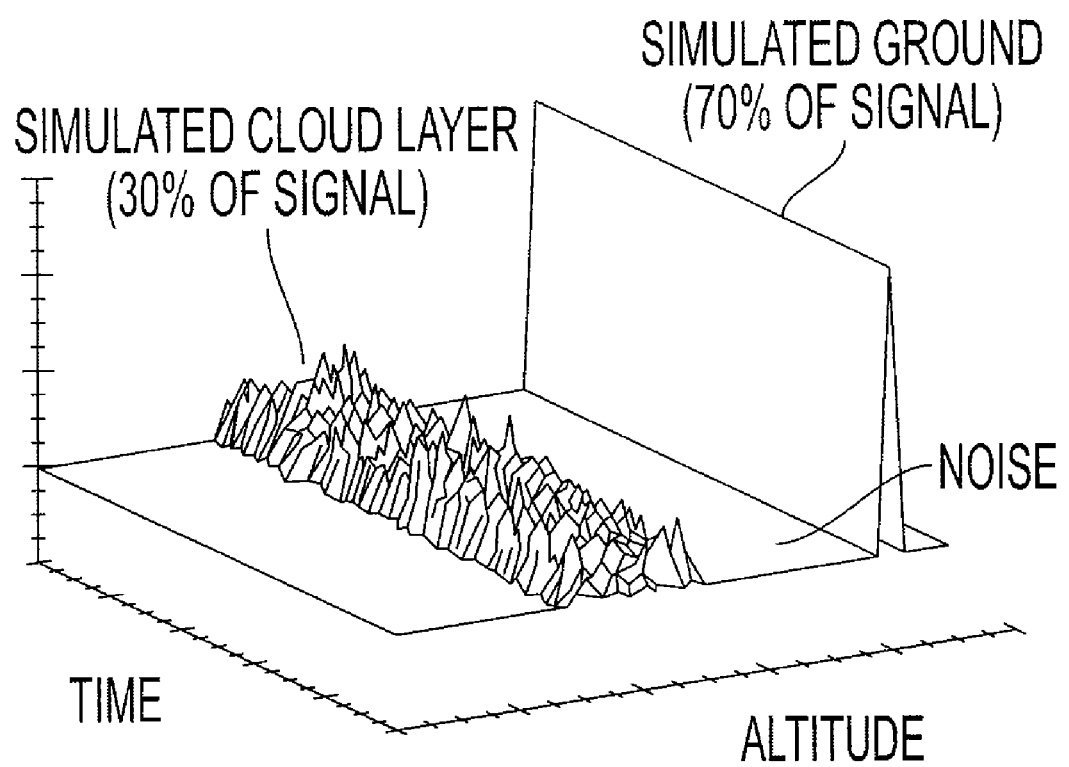
FIG. 4 shows a simulated cloud layer with a simulated ground return.

An investigation into the accuracy of the online/offline ratios using the stepped chirp modulation was conducted and suggests the following:

The exemplary sampling frequency $f_s$ of 1 MHz requires use of 16 bit sampling. Such digitization produces noise which was also simulated in the modeling of the results. In addition, a random noise component that corresponds to an SNR of 700 was also added to all sampled and emitted signals. Finally, a random multiple layer cloud layer was generated that produced a backscatter signal that is approximately 30% of the total lidar signal when combined with the ground scattered light. This is shown in FIG. 4, where the ground signal is 70% of the received signal and the simulated cloud layer is 30% of the received signal.

With the exemplary stepped chirp sweeps shown in FIGS. 1(a) and 1(b), a ground retrieval may be made at a resolution of just over 4 Hz (approximately >2 km resolution). In addition, the stepped chirp pulse may also be stepped up then down in a saw tooth pattern.

With the simulated analog to digital resolution and SNR random noise, the instantaneous random error on the online/offline retrieval. Overall, a standard deviation of slightly greater than 1% was obtained in the modeling investigation.

It will be appreciated, however, that any possible error from the approximation of Eqn. 29 may also add extra noise or even bias to the retrieval. Also, the use of a CW altimeter may add noise to the P'(t) signal, which may not be properly represented by the random number generator used in the investigation. Finally, the analysis also assumed that the cloud layer structure on each new retrieval is entirely random (hence, any autocorrelation in the result from sample to sample was not simulated). Also, it was assumed that the ground is a perfect Dirac delta function, whereas the real reflection from the ground may add extra noise terms.

Figure 5:
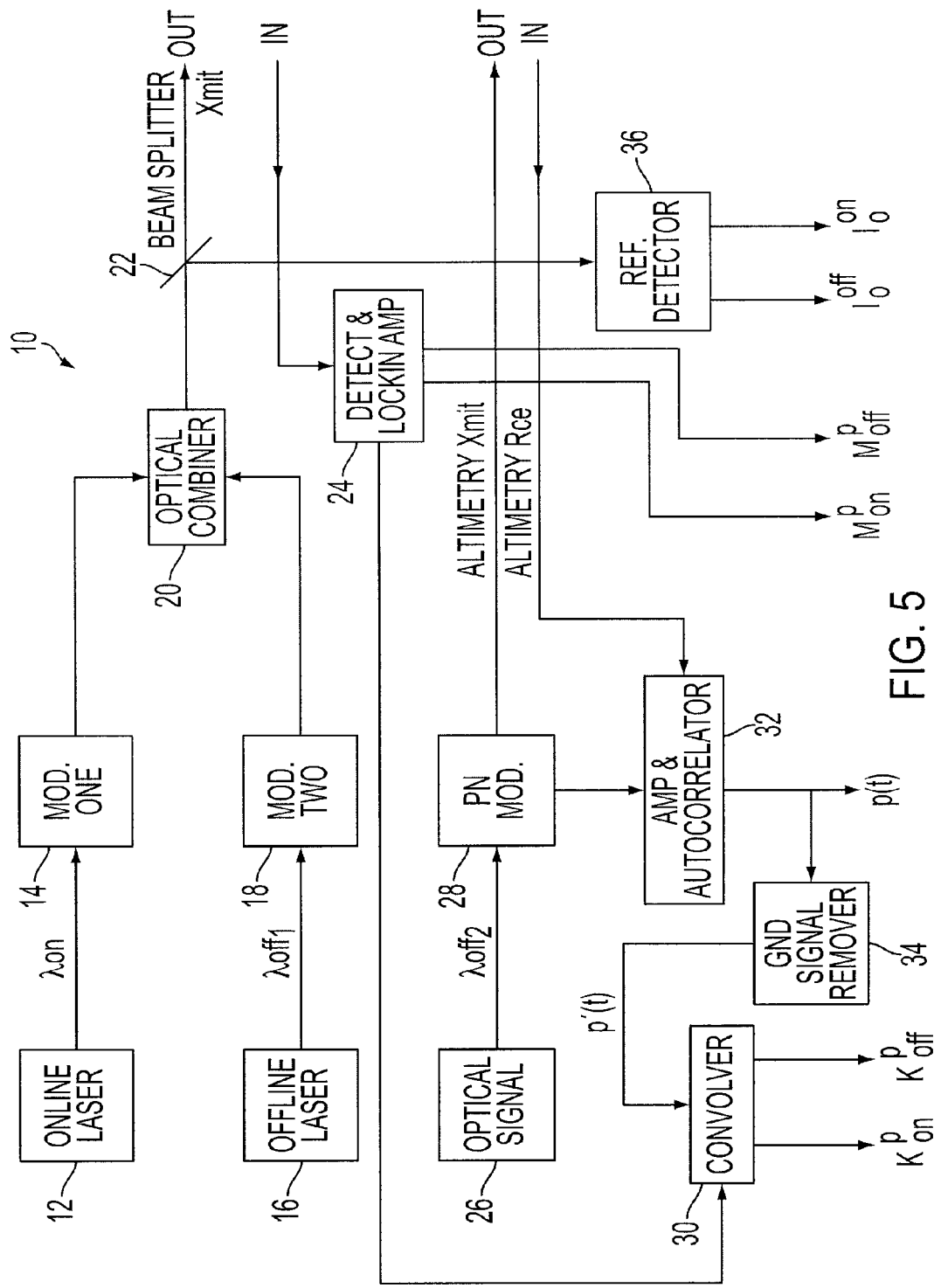
FIG. 5 is a block diagram of a system for assessing a column of gas in the atmosphere.
Figure 6:
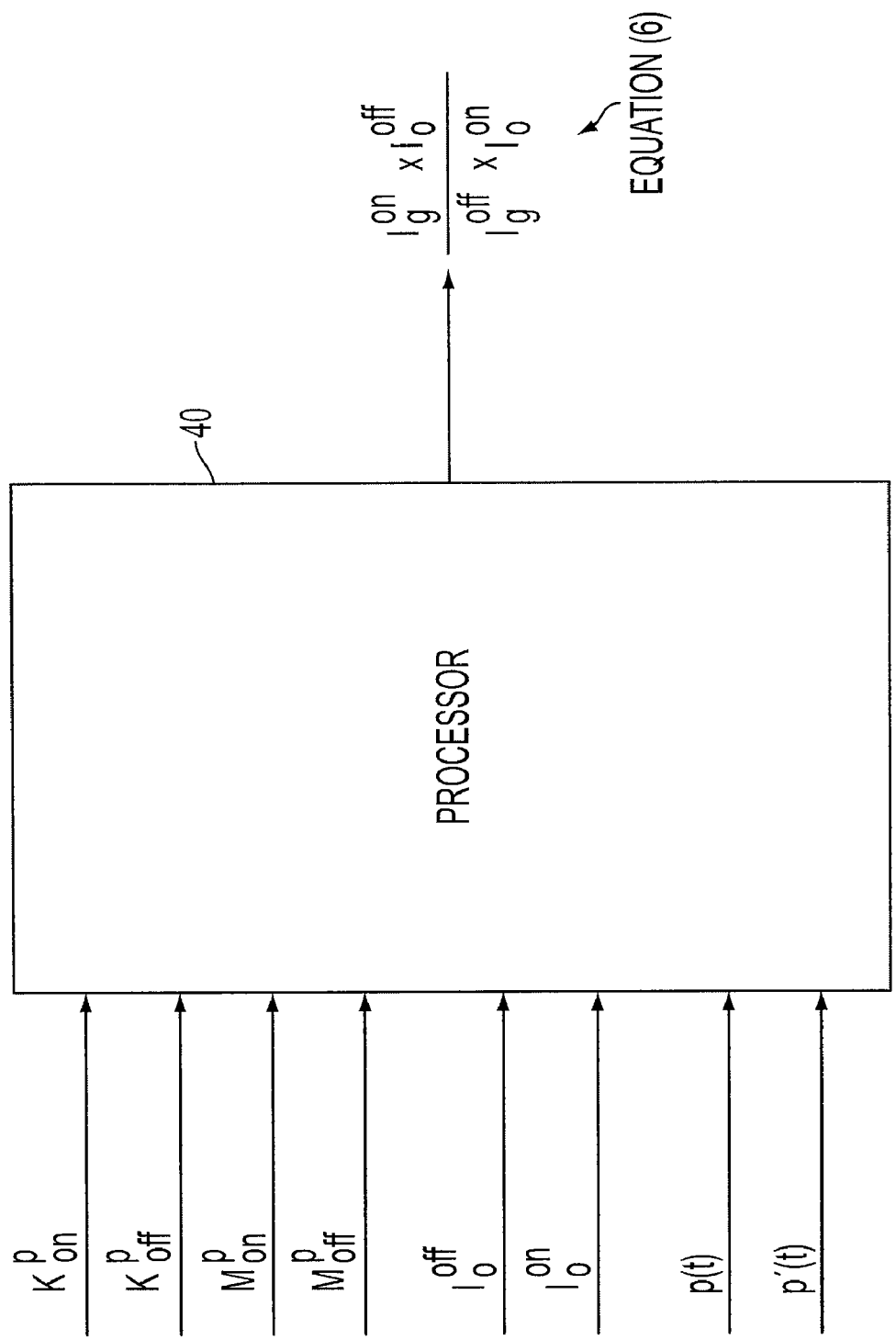
FIG. 6 is a continuation block diagram of FIG. 5, showing a processor(s) for the system of FIG. 5, which computes an output shown as Equation (6), in order to derive the density of a column of gas, in accordance with an embodiment of the present invention.

Referring now to FIGS. 5 and 6, an exemplary embodiment of the present invention is shown therein. As shown, system 10 includes online laser 12, offline laser 16 and optical signal transmitter 26. The online laser produces an online signal which may be absorbed by a gas (for example, carbon dioxide) at a wavelength $\lambda$on. Offline laser 16 produces an offline signal at a wavelength $\lambda \text{off}_1$, which is not absorbed by the gas (for example, carbon dioxide). The optical signal transmitter 26 produces yet another offline wavelength at $\lambda \text{off}_2$. It will be appreciated that although two offline optical transmitters are shown in FIG. 5, as offline laser 16 and optical signal transmitter 26, the present invention may include only one offline transmitter producing one offline wavelength signal, or two different offline wavelength signals.

The first modulator, designated as 14, modulates the $\lambda$on signal by a first stepped chirp sweep frequency signal. The second modulator, designated as 18, modulates the offline signal $\lambda \text{off}_1$ with a second stepped chirp sweep frequency signal. As shown in FIGS. 1(a) and 1(b), the stepped offline chirp frequency and the stepped online chirp frequency are different from each other. However, the steps of each chirp frequency in the first sweep are synchronized to the steps of each chirp frequency in the second sweep. This synchronization may be accomplished by a common clock signal.

The optical signal transmitter 26 also produces an optical offline signal at wavelength $\lambda \text{off}_2$, which is modulated by a pseudo-random generator, designated as 28. The pseudo-random generator 28 upon modulating the optical offline signal forms the transmitted altimetry data. Upon reception of the altimetry data, an amplifier and autocorrelator module, designated as 32, produces the altimetry data, referred to as P(t). It will be understood that although a pseudo random generator and autocorrelator are shown in FIG. 5, which form the received altimetry data, nevertheless, the optical signal may be modulated by a different type of modulation signal and detected by a different type of signal processor. The altimetry data, P(t), includes reflections from the ground and reflections from the cloud layers. The ground signal remover 34 removes the ground reflections from the altimetry data to form only the scattered noise from the cloud layers, designated at P'(t).

As further shown in FIG. 5, the online modulated chirp signal and the offline modulated chirp signal are combined by optical combiner 20 and transmitted through beamsplitter 22 and through the atmosphere to the ground surface, as a combined online and offline signal. The returned signal is detected and locked in by a detector and lock in amplifier residing in module 24, thereby forming two separate signals. The two signals are referred to herein as $M_{on}^P$ and $M_{off}^P$.

The transmitted signal is also sampled by beamsplitter 22 and reference detector 36 to produce the transmitted offline and online signals, referred to herein as $I_0^{off}$ and $I_0^{on}$ signals, respectively.

After detection and lock in by module 24, the resulting received signals are sent to convolving module 30, where the signals are convolved with the returned scattered noise from the altimetry data, namely P'(t). The convolving module forms two simulated signals, referred to herein as $K_{on}^P$ and $K_{off}^P$.

A single or parallel processor, designated as 40, which may be housed in system 10, receives various input signals produced by system 10, as shown in FIG. 6. As shown, the $K_{on}^P$ and $K_{off}^P$ signals, the $M_{on}^P$ and $M_{off}^P$ signals, the $I_0^{eff}$ and $I_0^{on}$, signals, and the P(t) and P'(t) signals are inputted into processor 40. The processor includes regression modules for performing the regressions of the $K_{on}^P$ and $K_{off}^P$ signals with the $M_{on}^P$ and $M_{off}^P$ signals, respectively. Results of the regressions are shown, as examples, in FIGS. 3(a)-3(d). It will be understood that convolving module 30 and the autocorrelation portion of module 32, as well as the ground signal remover module 34 may be incorporated into processor 40.

After recovering the scattered altimeter noise, regressing the Ms against the Ks, and determining the initial transmitted online and offline signals ($I_0^{off}$ and $I_0^{on}$ signals), processor 40 produces the results of Equation (6) as shown in FIG. 6. The results of Equation (6) is the desired result, from which the density of a column of gas may be determined.

Figure 7:
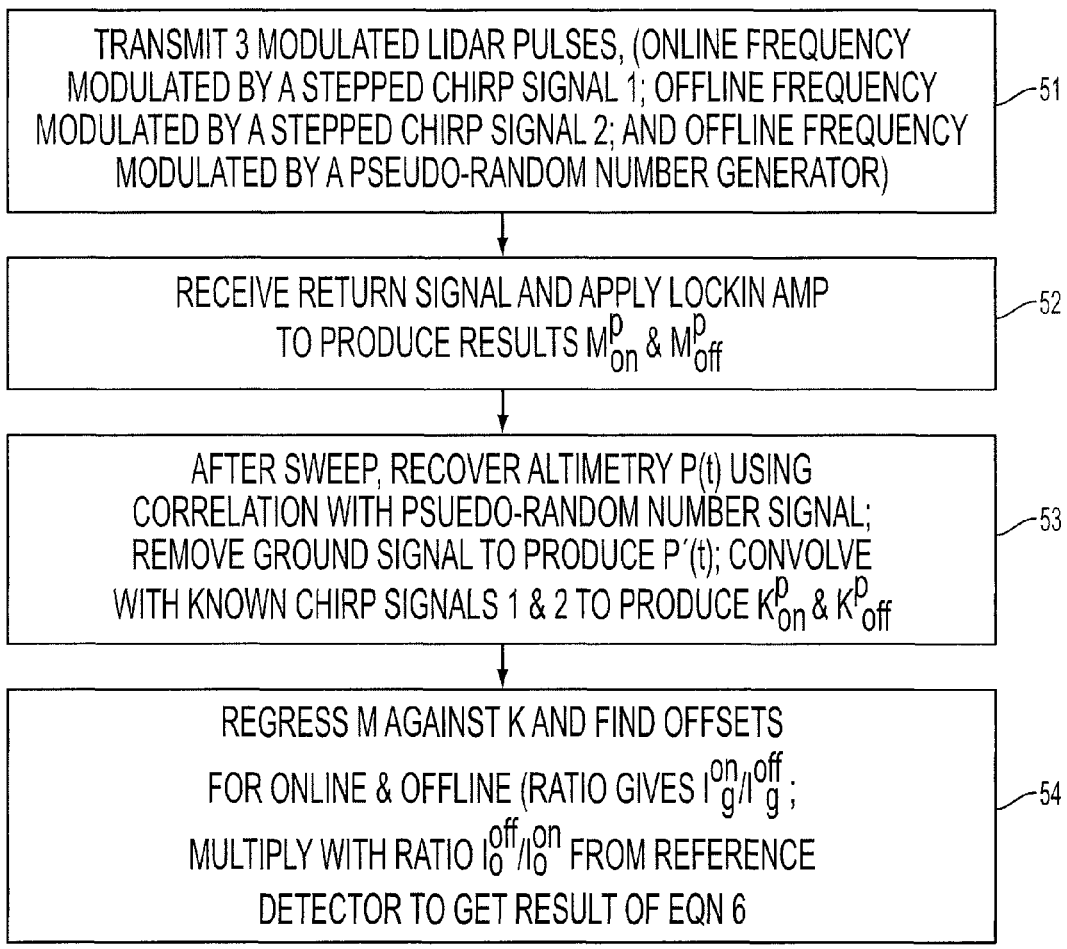
FIG. 7 is a block diagram of a method of the present invention for obtaining the results of Equation (6), from which a determination of the density of a column of gas is made, in accordance with an embodiment of the present invention.

Referring next FIG. 7, there is shown an exemplary method of the present invention. As shown, block 51 includes transmitting three modulated lidar signals. The first transmitted lidar signal is modulated by a first stepped chirp signal. The second transmitted lidar signal is modulated by a second stepped chirp signal. The third transmitted lidar signal is modulated by a pseudo random generator (for example). The first transmitted lidar signal is an online signal, and the second and third lidar signals are offline signals.

Block 52 receives and detects the returned signals using a detector and lock in amplifier to form the results of $M_{on}^P$ and $M_{off}^P$.

Block 53 recovers the altimetry data, P(t), using autocorrelation with the pseudo random coded signal. The ground signal is removed to produce only the scattered noise returned from the clouds, namely P'(t). The scattered noise is then convolved with the known first and second stepped chirp signals to form $K_{on}^P$ and $K_{off}^P$.

Block 54 performs regression of $M_{on}^P$ and $M_{on}^P$ against $K_{on}^P$ and $K_{off}^P$, respectively, thereby finding offsets for the online and offline signals. The formed ratio provides $I_g^{off}$ and $I_g^{on}$ signals. This ratio is next multiplied by the sampled initial transmitted signals, namely $I_0^{off}$ and $I_0^{on}$ signals, to obtain the results of Equation (6).

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A system for assessing a column of gas in an atmosphere comprising:
    an optical transmitter for transmitting (a) an online signal tuned to an online wavelength of gas, (b) an offline signal tuned to an offline wavelength of the gas, and (c) an optical signal for providing altimetry data,
    a modulator for modulating the online signal with a first stepped chirp waveform and modulating the offline signal with a second stepped chirp waveform, and
    a processor for assessing the column of gas, after receiving a returned online signal, a returned offline signal and a returned optical signal,
    wherein the first and second stepped chirp waveforms each includes finite steps, each step having a time period sufficiently long to allow for travel time to a ground surface and sampling time of return signals at a substantially fixed frequency, and each step having a different frequency.

2. The system of claim 1 including
    a lock-in amplifier for (a) multiplying a returned signal with the first stepped chirp waveform to obtain a detected online signal, and (b) multiplying the returned signal with the second stepped chirp waveform to obtain a detected offline signal, wherein the processor is configured to remove ground reflections from the optical signal to obtain scattered noise, and assess the column of gas based on the scattered noise.

3. The system of claim 2 wherein
the processor is configured to (a) multiply an estimated returned online signal with the first stepped chirp waveform to obtain a simulated cloud only online signal, and (b) multiply an estimated returned offline signal with the second stepped chirp waveform to obtain a simulated cloud only offline signal, and
the processor is configured to assess the column of gas by performing regression between the detected online and offline signals and the simulated online and offline signals.

4. The system of claim 1 wherein
the first and second stepped chirp waveforms each includes a frequency change based on a sampling frequency divided by a base 2 sampling pack.

5. The system of claim 1 wherein
the first and second stepped chirp waveforms each includes a sawtooth waveform having a period of approximately 0.25 seconds.

6. The system of claim 1 wherein
the first and second stepped chirp waveforms are synchronized to each other.

7. The system of claim 1 wherein the optical transmitter includes
an online laser for transmitting the online signal,
an offline laser for transmitting the offline signal, and
a pseudo random noise (PN) modulator for modulating the offline laser to transmit the optical signal.

8. The system of claim 1 including
a reference detector for sampling the online and offline signals upon transmission and obtaining a first ratio between the online and offline signals emitted from the optical transmitter ($I_0^{on}$ and $I_0^{off}$),
wherein the processor is configured to determine scattered noise returned by the optical signal,
the processor is configured to determine a second ratio between the online and offline signals returned from ground ($I_g^{on}$ and $I_g^{off}$), based on the scattered noise, and
the processor is configured to obtain density of the column of gas by multiplying the first ratio with the second ratio.

9. The system of claim 1 wherein
the column of gas includes carbon dioxide, and
the optical transmitter is housed in a satellite orbiting the earth.

10. A method of assessing a column of gas between an airborne platform and the earth, the method comprising the steps of:
(a) transmitting an online optical signal modulated by a first stepped chirp waveform;
(b) transmitting an offline optical signal modulated by a second stepped chirp waveform;
(c) transmitting an optical signal modulated by a pseudo random noise (PN) waveform;
(d) determining scattered noise returned by the PN modulated optical signal; and
(e) assessing the column of gas, based on the modulated online and offline optical signals and the scattered noise returned by the PN modulated optical signal;
wherein determining the scattered noise includes receiving the PN modulated optical signal including a ground return component and scattered noise from clouds, and removing the ground return component.

11. The method of claim 10 wherein steps (a) and (b) includes
modulating the online and offline optical signals with the first and second stepped chirp waveforms, respectively, each waveform having a step sufficiently long to allow for travel time to a ground surface and sampling time of return signals.

12. The method of claim 10 wherein
each waveform includes a stepped frequency sweep of approximately 25 KHz to 75 KHz.

13. The method of claim 10 wherein assessing the column of gas includes
convolving the modulated online and offline optical signals with the scattered noise returned by the PN modulated optical signal.

14. A method of assessing a column of gas through the atmosphere, including layers of clouds, the method comprising the steps of:
(a) transmitting, by a lidar system, an online signal having a wavelength absorbed by a gas and an offline signal having a wavelength not absorbed by the gas, in which the online signal is modulated by a first stepped chirp waveform and the offline signal is modulated by a second stepped chirp waveform;
(b) transmitting a PN modulated optical signal having an offline wavelength not absorbed by the gas;
(c) determining emitted radiances of the online signal and the offline signal, as $I_0^{on}$ and $I_0^{off}$, respectively;
(d) determining scattered noise returned from the layers of clouds by the transmitted PN modulated optical signal, as P'(t);
(e) determining received radiances of the online signal and the offline signal during each chirp step of the first and second stepped chirp waveforms, respectively, as $M_{on}^P$ and $M_{off}^P$;
(f) estimating radiances of the online signal and the offline signal during each chirp step of the first and second stepped chirp waveforms, respectively, as $K_{on}^P$ and $K_{off}^P$;
(g) regressing the $K_{on}^P$ and $K_{off}^P$ signals against the $M_{on}^P$ and $M_{off}^P$ signals, respectively;
(h) determining radiances from the ground for the online and offline signals, respectively, as $I_g^{on}$ and $I_g^{off}$, based on step (g); and
(i) characterizing the column of gas, after performing step (h).

15. The method of claim 14 wherein
characterizing the column of gas includes determining density of the column of gas.

16. The method of claim 14 wherein
step (f) of estimating includes convolving the scattered noise returned from the layers of clouds with (i) an estimated returned online signal, and (ii) an estimated returned offline signal.

17. The method of claim 14 wherein
step (g) of regressing is performed after performing steps (a), (b), (c) and (d).

18. The method of claim 14 wherein
the first and second stepped chirp waveforms includes a sawtooth, which is cycled at approximately 4 Hz.

* * * * *